United States Patent [19]

Hatakeyama

[11] 4,403,959

[45] Sep. 13, 1983

[54] COUPLING DEVICE FOR A DENTAL INSTRUMENT

[75] Inventor: Narito Hatakeyama, Ichikawa, Japan

[73] Assignee: Kabushiki Kaisha Yoshida Seisakusho, Tokyo, Japan

[21] Appl. No.: 288,824

[22] Filed: Jul. 31, 1981

[51] Int. Cl.³ .............................................. A61C 1/08
[52] U.S. Cl. ..................................... 433/126; 433/82; 285/316
[58] Field of Search .................... 433/126, 80, 82, 146; 285/316, 277

[56] References Cited

U.S. PATENT DOCUMENTS

| | | | |
|---|---|---|---|
| 3,295,868 | 1/1967 | Bac | 285/316 |
| 3,656,781 | 4/1972 | Paine et al. | 285/316 |
| 3,698,088 | 10/1972 | Austin, Jr. | 433/80 |
| 4,176,899 | 12/1979 | Betts | 285/316 |
| 4,217,101 | 8/1980 | Loge | 433/82 |

FOREIGN PATENT DOCUMENTS 244715 5/1947 Switzerland ........................ 433/126
389825 7/1965 Switzerland ........................ 433/126

*Primary Examiner*—John J. Wilson
*Attorney, Agent, or Firm*—Jordan and Hamburg

[57] ABSTRACT

In dental instruments such as a dental handpiece and a syringe, a coupling device for detachably connecting a hose portion, which supplies air or liquid to these instruments, to an instrument body. The coupling device comprises a sleeve fitted over the hose portion with a clearance formed therebetween, a ball-like stop member inserted into at least one opening formed in a peripheral surface at the front end of the sleeve and movable in a diametral direction of the sleeve, a connection cylinder having one end coaxially mounted on the rear end of the instrument body and inserted into the sleeve, and an operating ring fitted over the sleeve and movable in an axial direction of the sleeve.

10 Claims, 6 Drawing Figures

COUPLING DEVICE FOR A DENTAL INSTRUMENT

FIELD OF THE INVENTION

The present invention relates to a coupling device for a dental instrument such as a dental handpiece and a syringe, and more particularly to a connection and disconnection between an instrument body and a supply hose having one end connected to a source of air or liquid so as to supply air or liquid to the instrument body.

DESCRIPTION OF THE PRIOR ART

A dental handpiece is well known, for example, as disclosed in U.S. Pat. Nos. 2,945,299 and 3,324,553, which comprises a hollow cylindrical body, a head portion disposed at the foremost end of the cylindrical body, and a turbine disposed within the head portion or a motor disposed within the cylindrical body and driven by pressurized air and in which a mist is sprayed from the head portion towards a tooth to be treated, pressurized air and liquid are supplied from an air passage and a water passage, respectively, axially extending within the cylindrical body, and a bur or a treating drill is mounted on a rotational shaft driven by the motor or turbine. In such a dental handpiece, since the rotational shaft is rotated at a high speed of 150,000 rpm or more, the bur is mounted on the rotational shaft integrally. On the other hand, burs of various shapes must be used for dental treatment. Thus, it has been proposed heretofore that a handpiece is divided into two portions, a handpiece body provided at the foremost end thereof with a head portion, and a hose portion on which the other end of a supply hose is mounted, the supply hose having one end connected to a source of pressurized air or a source of cooling water, so that a plurality of handpiece bodies having burs of different shapes are prepared and a handpiece body according to a treatment mode is connected to the hose portion. In this case, a connection mechanism for simple and rapid replacement of the handpiece body relative to the hose portion is required, and the supply hose need be connected to the handpiece so that the supply hose may be fully rotated with respect to the axis of the handpiece for facilitating maneuverability during treatment.

To meet such requirements, West Germany Utility Model No. 7,729,110 (corresponding to U.S. Pat. No. 4,217,101) discloses a handpiece wherein a fitting recess is provided within a rear end of a handpiece body, and an insert cylinder fitted in the recess is provided in a hose portion in such a manner that the cylinder may be projected from the front end of a coupling. In this handpiece, at least one steel ball resiliently biased by means of a spring in an axial direction of the recess is received within the fitting recess, and when the insert cylinder is completely inserted into the fitting recess, an inner peripheral surface of the insert cylinder at which the steel ball is positioned is formed with an annular groove for receiving the steel ball. Accordingly, when the handpiece and the hose portion are connected, all that need be done is to insert the insert cylinder into the fitting recess until the steel ball comes into engagement with the annular groove, and when the handpiece body is separated from the hose portion, both may be pulled in a direction opposite each other. However, such connection between the handpiece body and the hose portion is accomplished only by means of the steel ball biased axially by the spring, and thus, when the spring becomes fatigued, a pressing force thereof to the steel ball becomes so weak as to separate the handpiece body from the hose portion only by application of a small force thereto.

On the other hand, as a dental instrument having an instrument body and a supply hose similar to the handpiece, there is proposed a dental syringe, for example, as disclosed in U.S. Pat. No. 3,698,088. This syringe comprises a cylinder body having a nozzle and a control element for controlling a supply passage for supplying a medical fluid and air and controlling the supply of such fluid and air, and a supply hose portion to which is connected the other end of a supply hose having one end connected to a supply source of the fluid or air so as to supply the fluid or air to the syringe body. As may be seen also from the aforesaid U.S. patent, it is normally designed so that the syringe body and the supply hose portion are integral with each other, and if the syringe body is in trouble, check and repairs are carried out after the other end of the supply hose has been disconnected from the supply source. Accordingly, even in the syringe, it is extremely convenient for maintenance and repairs of the syringe if the syringe body can be simply separated from the supply hose portion.

SUMMARY OF THE INVENTION

It is an object of the present invention to provide a coupling device for a dental instrument comprising an instrument body for dental treatment, and a supply hose portion to a rear end of which is connected one end of a supply hose for supplying water, a medical solution and air to the instrument body from a source of supply thereof, in which the instrument body may be connected or disconnected from the hose portion in an extremely simple manner, and when the instrument body is once connected to the hose portion, they may be connected and locked firmly.

It is a further object of the present invention to provide a coupling device for a dental instrument in which when an instrument body and a hose portion are once connected, they are connected relatively rotatably to render maneuverability during dental treatment easy, and gases or liquids from the hose connected to the rear end of the hose portion are securely supplied to the instrument body.

In accordance with the present invention, there is provided a coupling device for a dental instrument comprising a dental instrument body having a bur drive means driven by a fluid medium or a nozzle for supplying a fluid medium to a tooth to be treated, at the foremost end thereof, the instrument body having a first fluid passage for supplying said medium to the drive means or the nozzle disposed within a front half portion thereof and a fitting recess in communication with the first passage disposed within a rear half portion thereof; a hose portion having an insert cylinder inserted into the fitting recess disposed at the foremost end thereof, the hose portion having a hose for supplying the medium connected to a rear end thereof, the hose portion being interiorly formed with a second fluid passage to provide communication between the first passage and the supplying hose, the second fluid passage extending in an axial direction; and a coupling device for relatively rotatably and detachably connecting the instrument body with the hose portion; the coupling device comprising a sleeve fitted over the hose portion with a clearance formed therebetween, a ball-like stop member inserted into at least one opening bored in a peripheral surface on the front end of the sleeve and movable in a radial direction of the sleeve, the stop member having a larger diameter than a wall thickness of the sleeve, a connection cylinder inserted into the sleeve having an external diameter substantially equal to an internal diameter of the sleeve and having a front end coaxially mounted on the rear end of the instrument body, and an operating ring fitted over the sleeve and movable between a first position and a second position positioned axially of the sleeve with a clearance formed therebetween; the connection cylinder having an axial length enough to support the stop member at an outer peripheral surface of the rear end when the insert cylinder is inserted to a locking position of the fitting recess, the insert cylinder being formed in its outer peripheral surface with an annular groove to receive therein the stop member projected axially of the sleeve from the opening of the sleeve when the insert cylinder is at the locking position; the operating ring being formed in its inner peripheral surface with an annulr recess formed in the inner peripheral surface on the front end thereof in order that when the operating ring is positioned at the first position, the end of the stop member may be moved in a direction opposite to the axial direction so as to be positioned in the same plane as the inner peripheral surface of the sleeve, and an engageable annular surface axially extending adjacent the rear end of the annular recess and having a smaller diameter than that of the annular recess in order that when the operating ring is positioned at the second position, the lower end of the stop member is extended into the annular groove to lock a fitting condition between the instrument body and the hose portion.

The coupling device for a dental instrument in accordance with the present invention is designed so that a stop member supported on a sleeve of a coupling pipe so as to be movable in an axial direction of the sleeve is fitted in an annular groove of an insert cylinder inserted into a fitting recess of the instrument body, and an operating ring is moved towards the foremost end of the sleeve to prevent movement of the stop member in a direction opposite to the axial direction thereof, thereby locking connection between the instrument body and the hose portion. Accordingly, the instrument body may be connected to or disconnected from the hose portion only by axial movement of the operating ring, and positive connection between the instrument body and the hose portion may be assured even during the use for a long period of time.

In a preferable embodiment of the present invention, the coupling device further comprises a slide ring axially movably fitted in a clearance between an insert cylinder and a coupling pipe and a first spring inserted into an insert cylinder to normally bias the slide ring towards the foremost end of the insert cylinder. The slide ring is provided to support a stop member extended axially of the sleeve from an opening of the sleeve when the hose portion is separated from the instrument body, and move the slide ring towards the rear end of the sleeve against a bias force of the first spring by the rear end of the insert cylinder so that the stop member engages the annular groove of the insert cylinder, when the instrument body is connected to the hose portion. When the instrument body is separated from the hose portion, the slide ring is moved towards the foremost end by means of the first spring in response to the movement of the insert cylinder and thus the stop member will not be disengaged from the opening of the sleeve. With this arrangement, a movement amount of the stop member in an axial direction of the sleeve can be increased. That is to say, since when the instrument body is separated from the hose portion, the slide ring can prevent disengagement of the stop member, the movement of the stop member in an axial direction of the sleeve in the opening is merely limited, and the opening has a diameter equal to or slightly larger than that of the stop member so that when the instrument body is connected to the hose portion, an approximately half of the stop member may be engaged with the annular groove of the insert cylinder whereas the remaining half thereof engaged with the opening to secure a further positive connection therebetween.

In a further preferable embodiment of the present invention, an operating ring is normally biased towards the foremost end of a sleeve by means of a second spring retined within the sleeve. The operating ring has an annular recess and an engaging surface between which is formed with an inclined stepped portion so that when the instrument body is separated from the hose portion, the stop member comes into engagement with the inclined stepped portion to prevent the operating ring from being moved towards the front end of the sleeve by means of a second spring. The engaging surface is formed in the axial other end thereof with an inner flange-like stopper so that when the instrument body and the hose portion remain connected, it comes into engagement with the stop member to prevent the operating ring from being moved toward the front end by means of a second ring. By the provision of the second spring, when the instrument body is connected to the hose portion, all that need be done is to insert the insert cylinder into the fitting recess, thus requiring no operation of the operating ring. In this case, the operating ring may be used only when both elements are separated, and when they are separated, the operating ring may be slidably moved towards the rear end of the sleeve against the bias force of the second spring.

DESCRIPTION OF THE PREFERRED EMBODIMENTS

Figure 1:
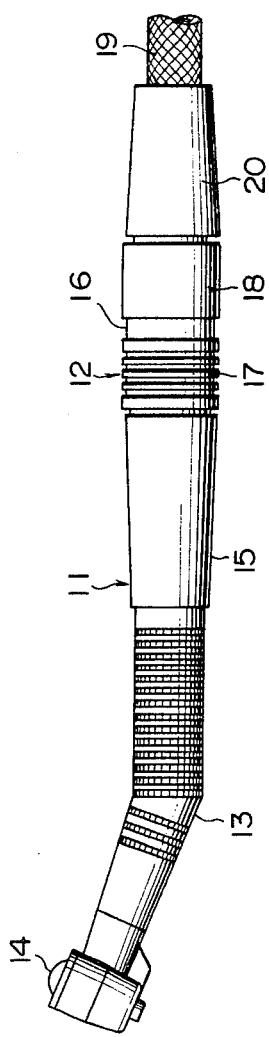
FIG. 1 is a side view showing one embodiment in its entirety, where a coupling device for a dental instrument in accordance with the present invention is applied to a dental handpiece.
Figure 2:
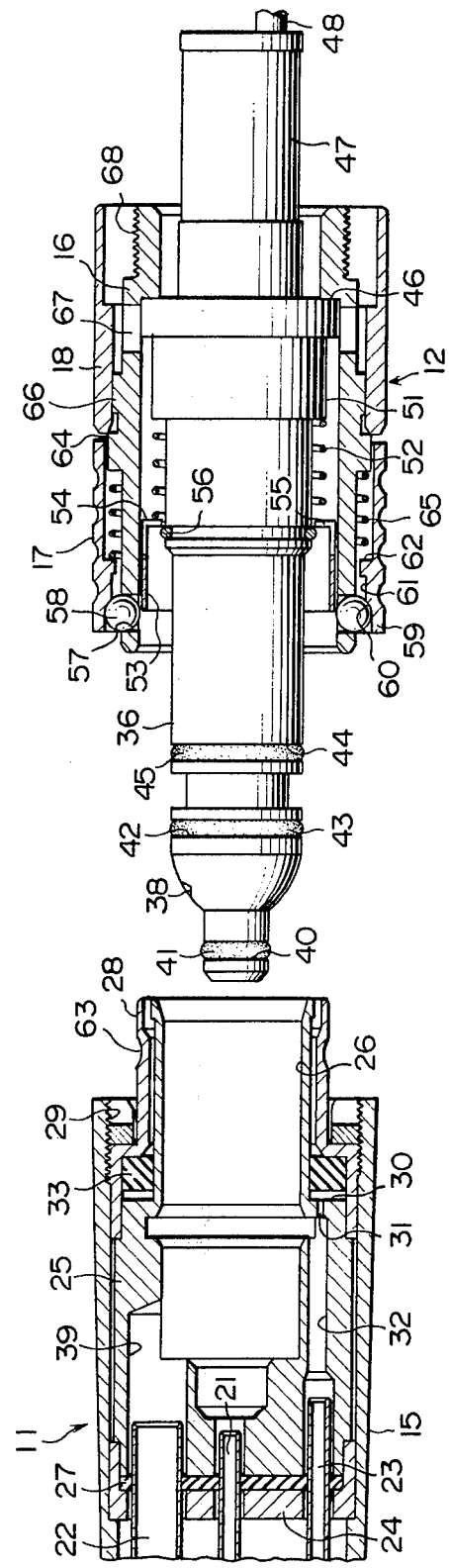
FIG. 2 is an exploded assembly view showing the construction of the dental handpiece of FIG. 1, with a part being shown cutaway.
Figure 3:
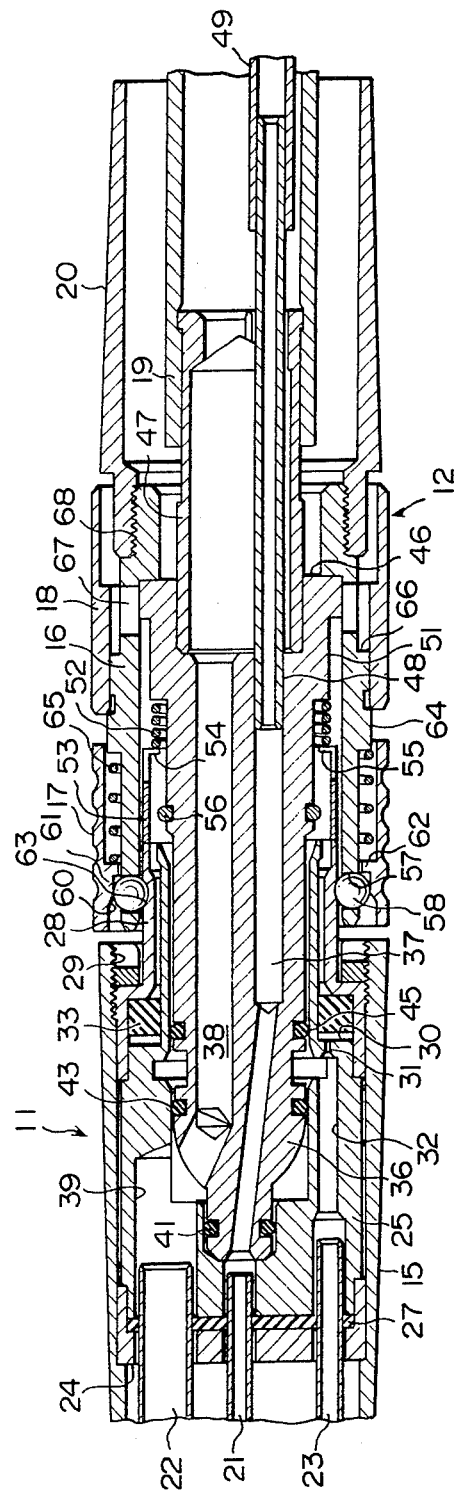
FIG. 3 is a longitudinal side view showing a connected condition between the handpiece of FIG. 1 and a hose portion.

FIGS. 1 through 3 show one embodiment in which the coupling device of the present invention is applied to a dental handpiece. The motor or air turbine mechanism driven by pressurized air is well known from the aforementioned U.S. Pat. Nos. 2,945,299 and 3,324,553 and therefore, the detailed construction and explanation will not be further made.

Referring now to FIG. 1, a dental handpiece comprises handpiece body generally designated by a reference numeral 11 and hose portion generally designated by a reference numeral 12 which is detachably connected to the body 11 and rotatably connected thereto. The handpiece body 11 comprises a hollow handle 13, a head 14 disposed at the foremost end of the handle 13 and a sleeve 15 disposed at the rear end of the handle 13, the head 14 being internally provided with a motor or an air turbien (not shown) driven by pressurized air. The hose portion 12 comprises a hollow coupling main pipe 16, an operating ring 17 axially movably fitted over the front end of the coupling main pipe 16 and a grip cover 18 fitted over the rear end of the coupling pipe 16. One end of a flexible hose 19 for feeding compressed air to drive the air turbine and water to cool a tooth to be treated to the head 14 is connected to the rear end of the coupling main pipe 16, a connection portion thereof being covered with a hose cover 20.

The detailed construction of the handpiece body 11 will be described hereinafter with reference to FIG. 2. A retaining disc 24 is inserted and secured within the sleeve 15 to support the respective end of a water supply duct 21 extending to the head 14 through the handle 13, an air supply duct 22 and an exhaust duct 23. A fitting cylinder 25 is inserted into the face side of the retaining disc 24 within the sleeve 15 opposite to the head 14. The fitting cylinder 25 has a fitting recess 26 in communication with the ducts 21, 22 and 23, and the front end of the cylinder 25 is in contact with the retaining disc 24 through a sealing disc 27. The fitting cylinder 25 is secured within the sleeve 15 by means of a connection pipe 28. That is, the connection pipe 28 is formed in an outer peripheral surface thereof with threads which are engaged with threads 29 provided in the inner surface of an opening at the rear end of the sleeve 15 so that the connection pipe 28 is screwed to lock the fitting cylinder 25 between the retaining disc 24 and the connection pipe 28. The respective end of the fitting cylinder 25 and the connection pipe 28 is axially projected from the other end of the sleeve 15. The fitting cylinder 25 has a shoulder 30 formed with a plurality of holes 31, and exhaust air from the exhaust duct 23 passes through an exhaust passage 32 disposed in the fitting cylinder 25, passes through a sound deadening porous packing 33 from the hoses 31 and then is discharged outside through a clearance between the fitting cylinder 25 and the connection pipe 28.

Next, the hose portion 12 will be described in detail with reference to FIG. 2, The hose portion 12 has an insert cylinder 36, the front half portion of which is rotatably and fittably connected to a fitting recess 26 of the fitting cylinder 25. The insert cylinder 36 is internally provided with a water passage 37 in communication with the water supply duct 21 and an air passage 38 in communication with the air supply duct 22, as shown in FIG. 3. For communication between the water supply passage 37 and the air duct 22 in the insert cylinder 36, the fitting cylinder 25 is provided with a communication passage 39. The insert cylinder 36 is provided in an outer periphery of the front end thereof with an annular groove 40 in which an O-ring 41 as a seal is fitted to positively feed water from the water passage 37 to the water supply duct 21. Similarly, there is provided an annular groove 42 in the outer periphery of the insert cylinder 36 positioned in the vicinity of the communication passage 39 when the insert cylinder 36 is fitted into the fitting recess 26 in order to feed air from the air passage 38 to the air supply duct 22, the groove 42 having an O-ring 43 fitted therein. Also, the insert cylinder 36 closer to the other end from the shoulder 30 of the fitting cylinder 25 is provided with an annular groove 44 in which an O-ring 45 is fitted. The rear end of the insert cylinder 36 extends into the coupling main pipe 16, and the rear end edge thereof bears on a shoulder 46 provided on the rear end of the coupling main pipe 16. On the rear end of the insert cylinder 36 is mounted a front end of a connection pipe 47 forming an air tank chamber to feed air to the air turbine in a stabilized state with pressure fluctuation of pressurized air relieved. The connection pipe 47 has a larger diameter than the air passage 38, the connection pipe has its front end communicated with the air passage 38 whereas the rear end communicated with the flexible hose 19. Inserted into the connection pipe 47 is a water pipe 48, a front end of which is in communication with the water passage 37, the water pipe 48 having the rear end extended from the rear end of the connection pipe 47. The water pipe 48 has its rear end connected to the front end of the water hose 49 extended into the flexible hose 19.

Next, a coupling mechanism between the handpiece 11 and in the hose portion 12 will be described. The insert cylinder 36 is formed at the rear end with a large diameter portion 51, and a coil spring 52 is fitted over the insert cylinder 36 in such a manner that the front end of the former may be secured by the large diameter portion 51. The rear end of the coil spring 52 engages an inner flange 54 provided on the other end of a slide ring 53 to normally bias the latter frontwardly. The slide ring 53 has an external diameter substantially equal to an internal diameter of the coupling main pipe 16 and the inner flange 54 has an internal diameter slightly larger than the external diameter of the insert cylinder, the slide ring 53 being slidable between the coupling main pipe 16 and the insert cylinder 36. The inner flange 54 is formed with a plurality of discharge ports 55 to discharge air passed through the clearance between the fitting cylinder 25 and the connection pipe 28. Forward movement of the slide ring 53 is limited by means of a stopper ring 56 disposed on the insert cylinder 36. The coupling main pipe 16 is formed in its front end with a plurality of through holes 57 in a circumferential direction, these through holes 57 respectively receiving therein steel balls 58 having a larger diameter than a wall thickness of the coupling main pipe 16. The steel balls 58, when the handpiece body 11 is not connected to the hose portion, are borned on the outer peripheral surface of the slide ring 53 and urged outwardly. An opening at the front end of the operating ring 17 has an inner peripheral surface formed with a thin wall thickness portion 59 for the ball 58, and an end opposite the open end of the portion 59 is formed with a thick wall thickness portion 61 through an inclined stepped portion 60. The thick wall thickness portion 61 has an axial length enough to support the steel ball 58, and the end of the thick wall thickness portion 61 opposite to the inclined stepped portion 60 is formed with a stopper 62 which extends axially. When the handpiece 11 is not connected to the hose portion 12, the steel ball 58 raised by the slide ring 53 bears on the inclined stepped portion 60 whereby the operating ring 17 is not disengaged from the coupling main pipe 16. On the other hand, the stopper 62 bears on the steel ball 58 when the handpiece body 11 is connected to the hose portion 12 to limit forward movement of the operating ring 17. The rear end of the connection pipe 28 in FIG. 2 has an external diameter substantially equal to the external diameter of the slide ring 53 so that when the handpiece body 11 is connected to the hose 12, the rear end portion of the connection pipe 28 has an axial length enough to be positioned below the steel ball 58. An annular groove 63 having a depth enough to move down the steel ball 58 in an axial direction by the thick wall portion 61 of the operating ring 17 when they are connected is provided in the outer peripheral surface of the rear end of the connection pipe 28. A large diameter portion 64 is formed in an outer peripheral surface of the coupling main pipe 16 at a position axially spaced apart from the stopper 62, and a coil spring is retained in the outer peripheral surface of the coupling main pipe 16 between the large diameter portion 64 and the stopper 62. The coil spring 65 has one end engaged with the stopper 62 and the other end engaging the large diameter portion 64, the coil spring 65 normally biasing the operating ring 17 forwardly.

The grip cover 18 has its front end engaged with the large diameter portion 64. and the rear end thereof is disposed in the outer peripheral surface of the coupling main pipe 16 in such a manner that the inner peripheral surface thereof is positioned in a spaced relation with the outer peripheral surface of the coupling main pipe 16 and secured to an annular support flange 66 having a smaller diameter than the large diameter portion 64. The space or clearance is provided to release outside air from the exhaust hole 55 of the slide ring 53 through the holes 67 disposed in the rear end of the coupling main pipe 16 in a suitably spaced relation. The coupling main pipe 16 has threads 68 formed in the outer peripheral surface at the rear end thereof, to which one end of the hose cover 20 is threaded and secured.

In a state where the handpiece body 11 is removed from the hose portion 12, the hose portion 12 is that as shown in FIG. 2, the slide ring 53 causes the steel ball 58 to be urged outwardly and the steel ball 58 is positioned at the thin wall thickness portion 59 of the operating ring 17. When the handpiece body 11 is connected to the hose portion 12 as shown in FIG. 3 from the above-described state, the insert cylinder 36 may be inserted into the fitting recess 26. Thereby, the connection pipe 28 urges the slide ring 53 against the coil spring 52, and the steel ball 58 is fallen into the annular groove 63 disposed in the connection pipe 28 for engagement therewith. Then, the inclined stepped portion 60 of the operating ring 17 is disengaged from the steel ball 58 and the operating ring 17 moves forward by the bias force of the coil spring 65. This forward movement of the operating ring 17 brings the steel ball 58 into engagement with the thick wall thickness portion 61 of the operating ring 17 and the steel ball 58 is urged in an axial direction. The forward movement of the operating ring 17 is stopped by engagement of the steel ball 58 with the stopper 62. As a result, the outward movement of the steel ball 58 is completely stopped and both will not be separated from each other even pulling them in a direction opposite to each other by carrying the handpiece body 11 and the grip cover 18. In this connected condition, the insert cylinder 36 is rotatably fitted into the fitting cylinder 25 through the O-rings 41, 43 and 45, and the coupling main pipe 16 is rotatably connected to the connection pipe 28.

The air fed to the flexible hose 19 passes through the air passage 38 and the air supplying duct 22 within the handpiece body 11 to drive the air turbine at the tip thereof. Pressurized air used to drive the air turbine then passes through the exhaust duct within the handpiece body 11, the exhaust passage 32 and the hole 31 and is discharged outside from the exhaust passage formed between the grip cover 18 and the hose cover 20 via the respective portion between the fitting cylinder 25 and the connection pipe 28, between the slide ring 53 and the insert cylinder 36, the discharge port 55 of the slide ring 53 and between the coupling main pipe 16 and the insert cylinder 36 and the hole 67 of the coupling main pipe 16. Water supplied from the water hose 49 is introduced into the water supplying duct 21 of the handpiece body 11 through the water passage 37 and is injected through the tip of the handpiece body 11.

Next, the case where the handpiece body 11 is separated from the hose portion 12 will be described. First, if the operating ring 17 is pulled rearwardly against the bias force of the coil spring 65, the thin wall thickness portion from the thick wall thickness portion 61 of the operating ring 17 is positioned on the steel ball 58 so that the steel ball 58 may be moved upward. When the handpiece body 11 is pulled forwardly from the above-mentioned state, the steel ball 58 is disengaged from the annular groove 63 to pull out the handpiece body 11. As the body 11 is pulled out, the the slide ring 53 is moved forward by means of the coil spring 52 to again receive the steel ball 58 at the outer peripheral surface thus preventing disengagement of the steel ball 58 as shown in FIG. 2.

Figure 4:
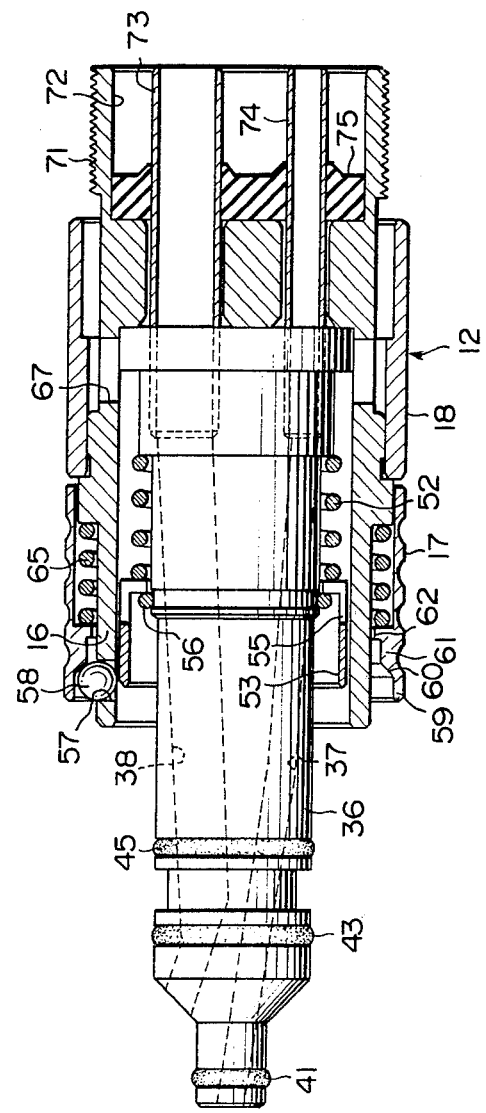
FIG. 4 is a side view showing another embodiment of a coupling pipe with a part thereof being cutaway.

FIG. 4 shows a further embodiment of the hose portion 12, in which similar parts to those of the abovedescribed embodiment are represented by like reference numerals, the description of which will not be further made. In this embodiment, the rear end of the coupling main pipe 16 is projected rearwardly from the rear end of the grip cover 18, the projected outer peripheral surface being provided with threads 71 for the hose cover, and a hollow portion 72 is formed in the rear end of the coupling main pipe 16 formed with said threads 71. In the first embodiment, previously described, the water pipe 48 within the insert cylinder 36 is received within the air supplying connection pipe 47 and the water hose 49 is received within the air supplying flexible hose 19. However, in this second embodiment, a water pipe 73 and an air pipe 74 are individually provided. That is, the front end of the water pipe 73 is connected to the rear end of the water passage 38 within the insert cylinder 36 whereas the front end of the air pipe 74 connected to the rear end of the air passage 37 within the cylinder 36, the respective end of the pipes 73 and 74 being exposed to the hollow portion 72 individually disposed within the rear end of the coupling main pipe 16. A seal packing 75 is fitted into the front end of the hollow portion 72. A water hose and an air hose though not shown are respectively connected to the rear ends of the water pipe 73 and the air pipe 74, respectively. Even in the case the water hose and the air hose are individually provided, connection can be done in a simple manner.

Figure 5:
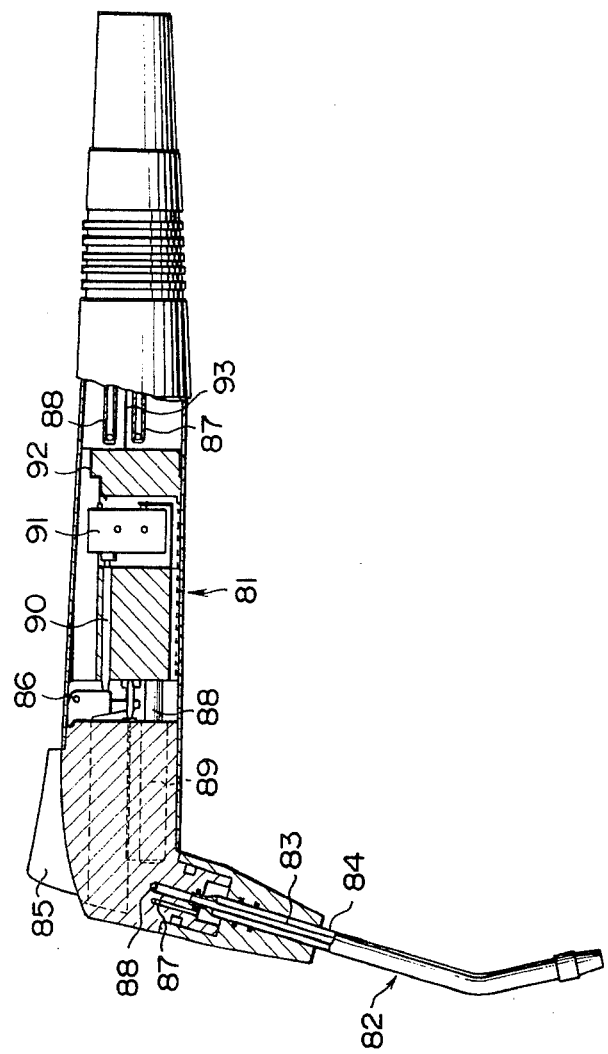
FIG. 5 is a side view showing one embodiment with a part being cutaway, where the coupling device of the present invention is applied to a dental syringe.
Figure 6:
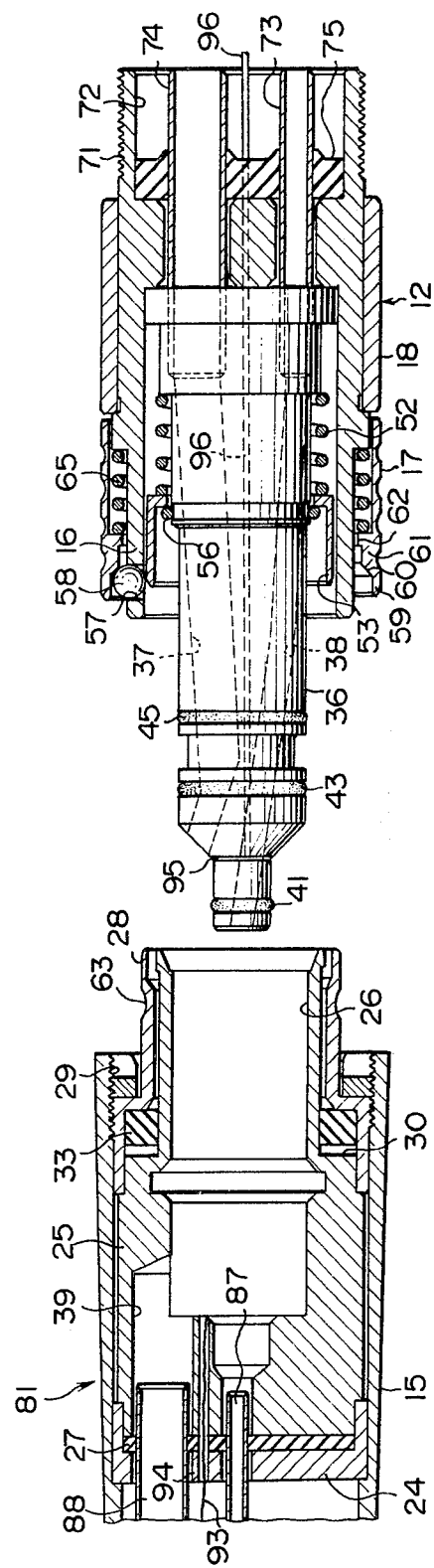
FIG. 6 is an exploded assembly view showing the construction of the dental syringe in FIG. 5 with a part being shown cutaway.

FIGS. 5 and 6 show one embodiment in which the coupling device of the present invention is applied to a dental syringe. Like components in the above-described embodiments are represented by like reference numerals, and the explanation therefor will not be made. A syringe body 81 has a nozzle 82 formed from a dual pipe, an inner pipe 83 being supplied with water or a medical fluid and an outer pipe supplied with air. In the syring body 81, a plurality of manual operating levers 85 are pivotally mounted by a pivot 86 so that when one operating lever is actuated, water or a medical fluid is provided through the nozzle 82 while when the other operating lever is actuated, air is provided therethrough. The inner pipe 83 is in communication with a liquid passage pipe 87 disposed within the syringe body 81 whereas the outer pipe 84 in communication with an air passage pipe 88 disposed within the syringe body 81. The air passage pipe 88 partly passes through a heater 89 so that air is heated by said heater 89. The heater 89 is controlled by means of a microswitch 91 turned on and off by an operating rod 90 operatively connected to the manual operating lever 85. This microswitch 91 is provided in an electric circuit block 92. A lead wire 93 having one end connected to the electric circuit block 92 has the other end exposed to the front end of the fitting recess 26 passing through the retaining disc 24, the sealing disc 27 and a hole 94 in communication with the fitting cylinder 25. When the hose portion 12 is connected to the syringe body 81, a conductive ring plate 95 is provided on the outer peripheral surface of the front end of the insert cylinder 36 in contact with the other end of the lead wire 93. One end of a power supply cord 96 is connected to the conductive ring plate 95, the other end thereof being connected to a power supply (not shown) through the insert cylinder 36. Accordingly, even if the syringe body 81 is rotated relative to the hose portion 12, electric connection between the hose portion 12 and the syringe body 81 is always secured positively. The mechanism for supplying air or liquid from the hose portion 12 to the syringe body 81 is the same as the embodiment previously described. The coupling mechanism is totally the same as the above-described embodiment as can be seen from FIGS. 5 and 6, and the description therefor will not be made.

What is claimed is:

1. A coupling device for a dental instrument comprising a dental instrument body having a drive means driven by a fluid medium, said instrument body having a first fluid passage for supplying said medium to said drive means disposed within a front half portion thereof and a fitting recess in communication with said first passage disposed within a rear half portion thereof; a hose portion having an insert cylinder inserted into said fitting recess disposed at the foremost end thereof, said hose portion having a supply hose for supplying said medium connected to a rear end thereof, said hose portion being interiorly formed with a second fluid passage to provide communication between said first passage and said supply hose, said second fluid passage extending in an axial direction; and a coupling device for detachably connecting said instrument body with said hose portion; said coupling device comprising a sleeve fitted over said hose portion, said sleeve having an opening, a ball-like stop member inserted into said opening and movable in a radial direction, said stop member having a larger diameter than the wall thickness of said sleeve, a connection cylinder inserted into said sleeve having an external diameter substantially equal to the internal diameter of said sleeve and having a front end coaxially mounted on the rear end of said instrument body, and an operating ring fitted over said sleeve and movable between a first position and a second position positioned axially of said sleeve with a clearance formed therebetween; said connection cylinder being formed on its outer peripheral surface with an annular groove to receive therein said stop member when said insert cylinder is inserted into said fitting recess into a locking position; said operating ring being formed in its inner periphery with a first annular surface at the front end thereof so that when said operating ring is positioned in said first position, the inner radial portion of said stop member is positioned in the same place as the inner peripheral surface of said sleeve, and a second annular surface on said operating ring having a smaller diameter than that of said first annular surface so that when said operating ring is positioned in said second position, the inner radial portion of said stop member extends into said annular groove to provide a lock fitting between said instrument body and said hose portion, said operating ring having an abutment which is engaged by said stop member when said operating ring is in said second position wherein the engagement of said abutment and said stop member determines said second position of said operating ring, said coupling device being released by manually grasping said operating ring to move the latter axially from said second position to said first position such that said abutment is disengaged from said stop member, said stop member being thereby released from said annular groove by said axial movement of said operating ring to thereby permit detachment of said instrument body from said hose portion.

2. The coupling device for a dental instrument according to claim 1 further comprising a slide ring inserted into said sleeve and having an external diameter substantially equal to the internal diameter of said sleeve, a first spring means for resiliently biasing said slide ring towards the front end of said sleeve, and a stopper disposed on said insert cylinder in order to control the amount of movement of said slide ring towards said front end, whereby when said instrument body is separated from said hose portion, the inner radial portion of said stop member is supported by the outer peripheral surface of said slide ring, and when said hose portion is connected to said instrument body, said slide ring is slid towards the rear end of said sleeve by the rear end of said connection bylinder.

3. The coupling device for a dental instrument according to claim 1 further comprising a second spring means inserted over said sleeve to resiliently bias said operating ring in the direction of said first position, whereby when said hose portion is connected to said instrument body when said insert cylinder is inserted to said locking position within said fitting recess, said operating ring automatically assumes said second position.

4. The coupling device for a dental instrument according to claim 1, wherein the rear end of said sleeve is provided with threads for mounting a hose cover for said supplying hose.

5. The coupling device for a dental instrument according to claim 1, wherein a fluid pipe having one end connected to said second fluid passage is provided on the rear end portion of said insert cylinder, said supply hose being connected to said fluid pipe.

6. A coupling device for a dental instrument comprising a dental instrument body having a nozzle for supplying a fluid medium to a tooth to be treated at the foremost end thereof, said instrument body having a first fluid passage for supplying said medium to said nozzle disposed within a front half portion thereof and a fitting recess in communication with said first passage disposed within a rear half portion thereof; a hose portion having an insert cylinder inserted into said fitting recess disposed at the foremost end thereof, said hose portion having a supply hose for supplying said medium connected to a rear end thereof, said hose portion being interiorly formed with a second fluid passage to provide communication between said first passage and said supply hose, said second fluid passage extending in an axial direction; and a coupling device for detachably connecting said instrument body with said hose portion; said coupling device comprising a sleeve fitted over said hose portion, said sleeve having an opening, a ball-like stop member inserted into said opening and movable in a radial direction, said stop member having a larger diameter than the wall thickness of said sleeve, a connection cylinder inserted into said sleeve having an external diameter substantially equal to the internal diameter of said sleeve and having a front end coaxially mounted on the rear end of said instrument body, and an operating ring fitted over said sleeve and movable between a first position and a second position positioned axially of said sleeve with a clearance formed therebetween; said connection cylinder being formed on its outer peripheral surface with an annular groove to receive therein said stop member when said insert cylinder is inserted into said fitting recess into a locking position; said operating ring being formed in its inner periphery with a first annular surface at the front end thereof so that when said operating ring is positioned in said first position, the inner radial portion of said stop member is positioned in the same place as the inner peripheral surface of said sleeve, and a second annular surface on said operating ring having a smaller diameter than that of said first annular surface so that when said operating ring is positioned in said second position, the inner radial portion of said stop member extends into said annular groove to provide a lock fitting between said instrument body and said hose portion, said operating ring having an abutment which is engaged by said stop member when said operating ring is in said second position wherein the engagement of said abutment and said stop member determines said second position of said operating ring, said coupling device being released by manually grasping said operating ring to move the latter axially from said second position to said first position such that said abutment is disengaged from said stop member, said stop member being thereby released from said annular groove by said axial movement of said operating ring to thereby permit detachment of said instrument body from said hose portion.

7. The coupling device for a dental instrument according to claim 6, further comprising a slide ring inserted into said sleeve and having an external diameter substantially equal to the internal diameter of said sleeve, a first spring means for resiliently biasing said slide ring towards the front end of said sleeve, and a stopper disposed on said insert cylinder in order to control the amount of movement of said slide ring towards said front end, whereby when said instrument body is separated from said hose portion, the inner radial portion of said stop member is supported by the outer peripheral surface of said slide ring, and when said hose portion is connected to said instrument body, said slide ring is slid towards the rear end of said sleeve by the rear end of said connection bylinder.

8. The coupling device for a dental instrument according to claim 6, further comprising a second spring means inserted over said sleeve to resiliently bias said operating ring in the direction of said first position, whereby when said hose portion is connected to said instrument body when said insert cylinder is inserted to said locking position within said fitting recess, said operating ring automatically assumes said second position.

9. The coupling device for a dental instrument according to claim 6, wherein the rear end of said sleeve is provided with threads for mounting a hose cover for said supplying hose.

10. The coupling device for a dental instrument according to claim 6, wherein a fluid pipe having one end connected to said second fluid passage is provided on the rear end portion of said insert cylinder, said supply hose being connected to said fluid pipe.

* * * * *